US00PP34346P2

(12) United States Plant Patent
Chen et al.

(10) Patent No.: US PP34,346 P2
(45) Date of Patent: Jun. 14, 2022

(54) ***HEDYCHIUM* PLANT 'CHEN XI'**

(50) Latin Name: ***Hedychium* hybrid**
Varietal Denomination: CHEN XI

(71) Applicant: Guangzhou Architecture and Landscape Gardening Co., LTD, Guangzhou (CN)

(72) Inventors: Shiren Chen, Guangzhou (CN); Cong Tang, Guangzhou (CN); Junlin Ye, Guangzhou (CN)

(73) Assignee: Guangzhou Architecture & Landscape Co., Ltd

( * ) Notice: Subject to any disclaimer, the term of this patent is extended or adjusted under 35 U.S.C. 154(b) by 0 days.

(21) Appl. No.: 17/345,416

(22) Filed: Jun. 11, 2021

(51) Int. Cl.
*A01H 5/12* (2018.01)
*A01H 6/02* (2018.01)

(52) U.S. Cl.
USPC ..... Plt./373

(58) Field of Classification Search
USPC ..... Plt./373
See application file for complete search history.

*Primary Examiner* — Karen M Redden

(57) ABSTRACT

A new and distinct cultivar of *Hedychium* plant named 'CHEN XI' is disclosed characterized by robust plants with resistance to *Pyricularia zingiberi* (Ginger Blast). Inflorescences are dense and composed of attractive salmon and yellow flowers with orange-red anthers. The new variety is useful as an ornamental plant in warm, wet climates.

3 Drawing Sheets

Latin name of the genus and species: *Hedychium* hybrid. Variety denomination: 'CHEN XI'.

BACKGROUND OF THE INVENTION

The new cultivar, *Hedychium* 'CHEN XI', is the product of a planned breeding program. The intent of the breeding program was to produce new ornamental ginger varieties for landscape purposes with improved resistance to diseases and pests in hot, wet climates. The new variety originated from a cross pollination of an unpatented, seed parent, *Hedychium coronarium* 'White Ginger' with the pollen parent an unpatented, unnamed variety of *Hedychium coccienum* x *gardnerianum*. The cross pollination was made during March of 2004 in Guangdong Province, China at a research nursery. The new cultivar 'CHEN XI' was selected in December of 2007 at the same location.

Asexual reproduction of the new cultivar 'CHEN XI' was first performed by division in Guangdong Province at a research nursery May of 2008. *Hedychium* 'CHEN XI' has since produced multiple generations and has shown that the unique features of this cultivar are stable and reproduced true to type.

SUMMARY OF THE INVENTION

The cultivar 'CHEN XI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CHEN XI'. These characteristics in combination distinguish 'CHEN XI' as a new and distinct *Hedychium* cultivar:

1. Usefulness as landscape plant in warm and wet climates.

2. Strong plants resistant to *Pyricularia zingiberi* (ginger blast).
3. Ornamental flowers of salmon and yellow with orange-red anthers.
4. Densely flowering inflorescences.

PARENTAL COMPARISON

Plants of the new cultivar 'CHEN XI' are similar to plants of the seed parent in most horticultural characteristics. However, plants of the new cultivar 'CHEN XI' differ in the following:

1. *Hedychium* 'CHEN XI' produces inflorescences of salmon and yellow; the seed parent produces white inflorescences.

Plants of the new cultivar 'CHEN XI' are similar to the pollen parent in most horticultural characteristics. However, plants of the new cultivar 'CHEN XI' differ in the following:

1. *Hedychium* 'CHEN XI' ornamental petaloids not found on the pollen parent.
2. Lateral corolla lobes and the labellum of *Hedychium* 'CHEN XI' are darker in color than those of the pollen parent.

COMMERCIAL COMPARISON

The new cultivar 'CHEN XI' can be compared to the unpatented commercial variety *Hedychium coccienum* 'Anne Bishop'. Plants of the new cultivar 'CHEN XI' differ in the following:

1. Plants of *Hedychium* 'CHEN XI' are shorter than plants of 'Anne Bishop'.
2. Individual flowers of *Hedychium* 'CHEN XI' are larger than flowers of 'Anne Bishop'.

BRIEF DESCRIPTION OF THE PHOTOGRAPHS

The accompanying photographs illustrate in full color typical plants of 'CHEN XI' grown outdoors, in the ground in Guangdong Province, China. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Hedychium* plant. Temperatures ranged from approximately 12° C. to 38° C. night and day. No artificial light, photoperiodic treatments or chemical treatments were given to the plants.

DETAILED BOTANICAL DESCRIPTION

Figure 1:
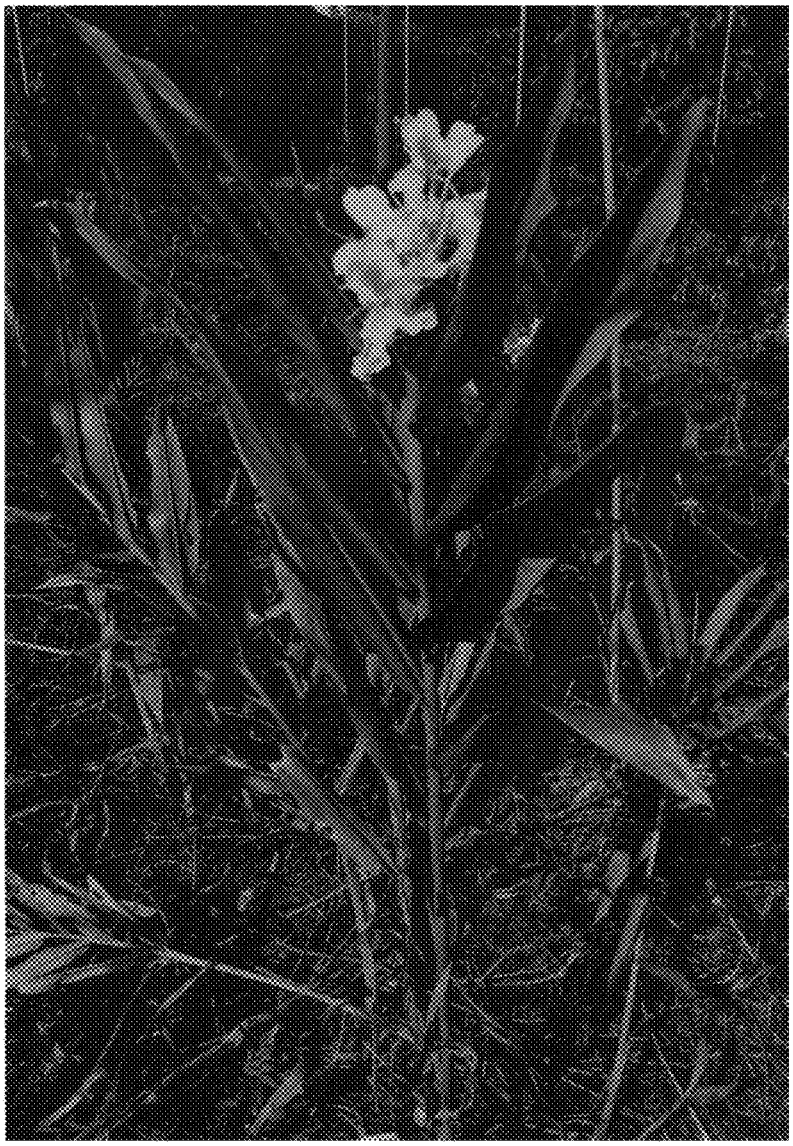
FIG. 1 illustrates in full color a typical of plant of *Hedychium* 'CHEN XI' at approximately 12 months.
Figure 2:
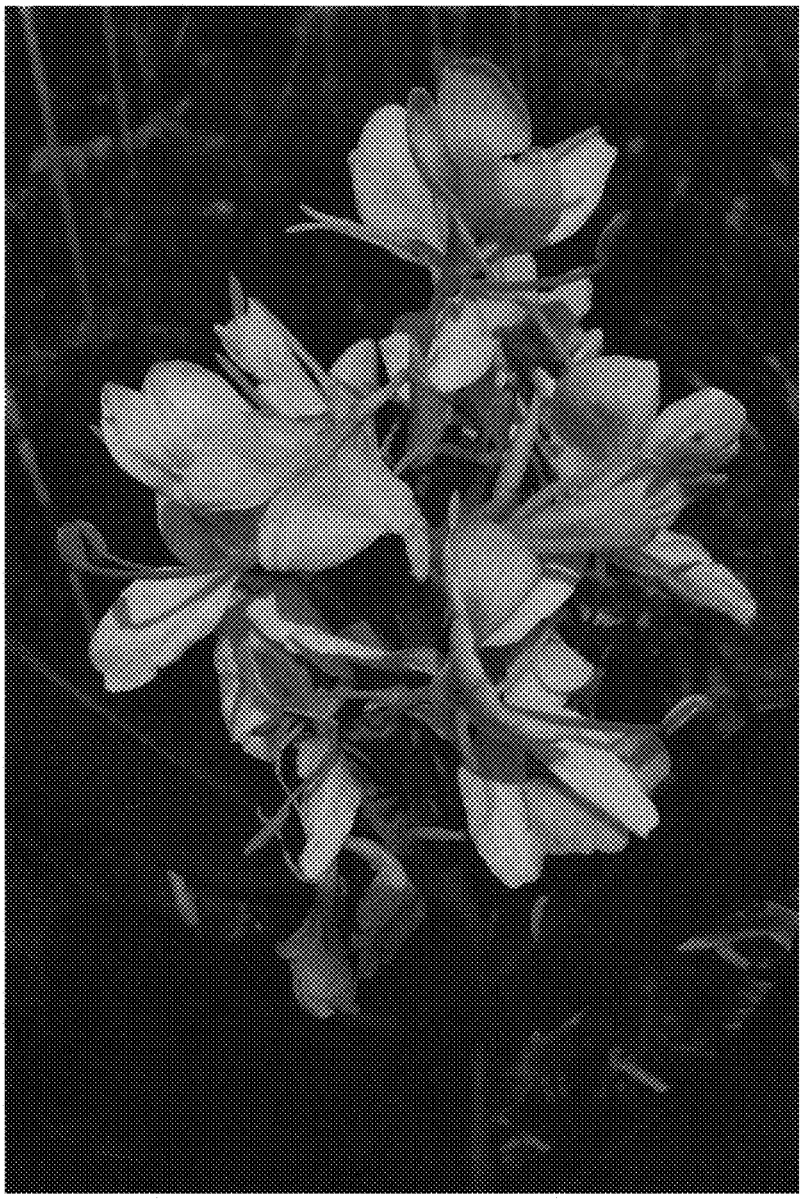
FIG. 2 illustrates in full color a typical inflorescence of *Hedychium* 'CHEN XI'.
Figure 3:
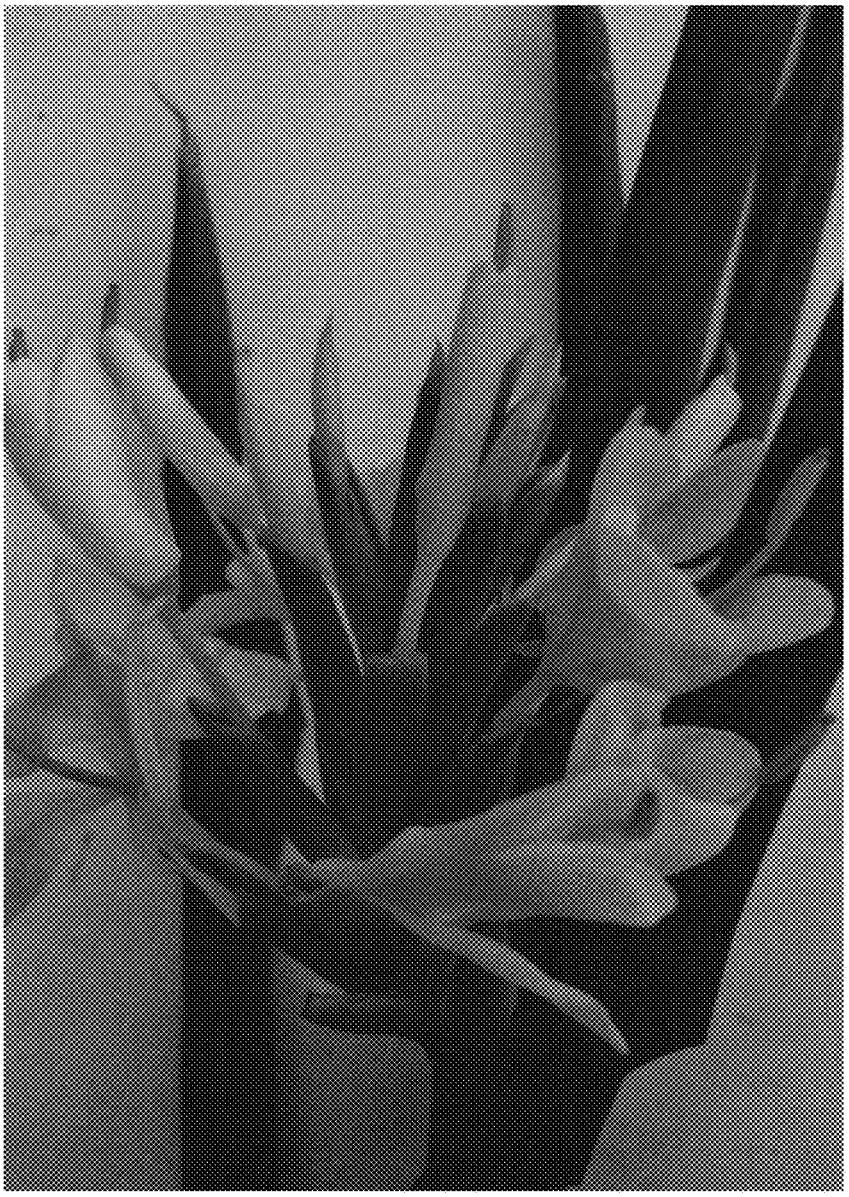
FIG. 3 illustrates in full color typical flowers of *Hedychium* 'CHEN XI'.

In the following description, color references are made to The Royal Horticultural Society Colour Chart, 2001, except where general terms of ordinary dictionary significance are used. The following observations and measurements describe 'CHEN XI' plants in a commercial greenhouse in Guangdong Province, China. Average day temperature was around 25° C.; average night temperature was around 18° C. No artificial light, photoperiodic treatments or chemical treatments were given to the plants. Natural light conditions were full sunlight. Measurements and numerical values represent averages of typical plant types. Measurements were taken during November of 2020.

Botanical classification: *Hedychium* hybrid 'CHEN XI'.

PROPAGATION

Type of propagation typically used: Division from side shoots. About 7 days at temperatures above 15° C.

PLANT

Age of plant described: Approximately 12 months.

Container size of the plant described: Field planted.

Growth habit: Tropical and subtropical perennial composed of an herbaceous pseudostem. Columnar in shape. Flowering from July until December with the most blooms occurring September through November.

Height: Average range 135 to 150 cm.

Plant spread: Approximately 50 cm.

Growth rate: Moderate.

Branching characteristics: No branching.

Root description: Cylindrical rhizomes. 30 to 50 cm long, 5 mm in diameter. Fleshy, colored near Yellow-White 158B.

FOLIAGE

Leaf:

*Arrangement.*—Alternate, single.

*Average length.*—Average 40 cm.

*Average width.*—7.0 cm.

*Shape of blade.*—Lanceolate.

*Apex.*—Acute.

*Base.*—Wedge-shaped.

*Margin.*—Entire.

*Attachment.*—Sessile sheath.

*Texture of top surface.*—Glabrous, leathery.

*Texture of bottom surface.*—Glabrous. Main vein has a slight pubescence.

*Appearance of top surface.*—Matte.

*Appearance of bottom surface.*—Matte.

*Color.*—Young foliage upper side: Near RHS Green 141C. Young foliage, under side: Near RHS Green 137C. Mature foliage upper side: Near RHS Green 141C. Mature foliage, under side: Near RHS Green 137C.

*Venation.*—Type: Linear. Venation color upper side: Near Green 138C. Venation color under side: Near Green 137C.

Sheath:

*Average length.*—Approximately 1 cm.

*Average diameter.*—Approximately 5 mm.

*Color.*—Upper surface: Near Yellow-Green N144B. Lower surface: Near Yellow-Green N144B.

*Texture.*—Glabrous.

FLOWER

Natural flowering season: Flowering from July until December with the most blooms occurring September through November.

Inflorescence type and habit: Short spicate, typically with 60 to 70 flowers. 1 inflorescence per plant. Individual flowers papilionaceous, held upright.

Inflorescence longevity as a cut flower: 4 to 5 days.

Flower longevity on plant: Individual flower 1 day.

*Total inflorescence size.*—Height: Approximately 12 to 15 cm. Width: Approximately 10 cm.

*Corolla.*—Arrangement: Papilionaceous. Longevity: 1 day. Size: Length: Approximately 8 cm. Width: Approximately 4.5 cm to 5 cm. Tube Length: Approximately 4.5 cm. Tube Diameter: Approximately 0.2 cm. Throat Diameter: Approximately 0.2 cm.

Lateral corolla lobe:

*Quantity.*—3.

*Margin.*—Entire.

*Shape.*—Narrow spatulate.

*Apex.*—Gently tapering.

*Base.*—Fused.

*Texture.*—Glabrous all surfaces.

*Length.*—3 cm.

*Width.*—6 mm.

*Color.*—When opening: Color, upper surface: Yellow-Orange 15B. Color, under surface: Yellow-Orange 15B. Fully opened: Color, upper surface: Yellow-Orange 15B. Color, under surface: Yellow-Orange 15B. Color Changes when Aging: Near RHS Red-36C all surface.

*Throat color.*—Near RHS Orange-Red 35B.

*Tube color.*—Near RHS Yellow-Orange 22C, interior and exterior.

Lateral petaloids (staminal petaloids):

*Arrangement.*—Opposite.

*Quantity.*—2.

*Length.*—3.0 cm.

*Width.*—1.2 cm.

*Shape.*—Elongated ovate.

*Margin.*—Entire.

*Apex.*—Obtuse.

*Base.*—Truncate.

*Texture.*—Glabrous all surfaces. Color: When opening: Upper surface: Yellow-Orange 16D. Under surface: Yellow-Orange 16D. Fully opened: Upper surface: Yellow-Orange 16D. Under surface: Yellow Orange 16D.

Labellum:

*Placement.*—At the apex of the flower.

*Quantity.*—1, fused only at lowermost base, forming the appearance of 2.

*Length.*—3.0 cm.

*Width.*—1.8 cm.

*Shape.*—Overall spatulate, 2 ovate lobes, fused only at very base.

*Margin.*—Entire.

*Apex.*—Obtuse.

*Base.*—Truncate.

*Texture.*—Glabrous all surfaces. Color: When opening: Upper surface: Yellow-Orange 16D. Under surface: Yellow-Orange 16D. Fully opened: Upper surface: Yellow-Orange 16D. Under surface: Yellow-Orange 16D.

Sepals:

*Quantity.*—1, covering bud, then shriveling.

*Length.*—2.8 cm.

*Width.*—6 mm.

*Shape.*—Ligulate.

*Apex.*—Gently tapering.

*Margin.*—Entire.

*Texture.*—Glabrous and fleshy all surfaces.

*Color.*—Upper Surface: Near Yellow-Green 145D. Under Surface: Near Yellow-Green 145D.

Bud: (near opening):

*Shape.*—Cylindrical ovate.

*Length.*—Approximately 5 cm.

*Diameter.*—Approximately 7 mm.

*Texture.*—Glabrous.

*Color.*—Near Yellow 13B.

Peduncle:

*Length.*—Average 1.5 cm.

*Width.*—Average 1.0 cm.

*Strength.*—Very strong.

*Texture.*—Glabrous.

*Color.*—Near RHS Yellow-Green 144C.

Pedicels:

*Length.*—Approximately 1.5 cm.

*Width.*—Approximately 1.0 cm.

*Strength.*—Moderate.

*Texture.*—Glabrous.

*Color.*—Near RHS Yellow-Green 144C.

*Angle.*—Upright.

Floral bracts:

*Quantity.*—2.

*Length.*—Approximately 3.2 cm.

*Width.*—Approximately 2.0 cm.

*Strength.*—Moderate.

*Texture.*—Glabrous, leathery.

*Color.*—Near RHS Green 143C.

Fragrance: Moderately weak.

REPRODUCTIVE ORGANS

Stamens: (Androecium).

*Number.*—Average 1.

*Filament length.*—Approximately 3.0 cm.

*Filament color.*—Near RHS Orange-Red 35B.

*Anther length.*—8 mm.

*Anther color.*—Near RHS Orange-Red 35A.

*Anther shape.*—Elliptic.

*Pollen color.*—Near RHS Yellow-White 158D.

*Pollen quantity.*—Scant.

Pistil: (Gynoecium).

*Number.*—1.

*Length.*—Approximately 3.5 cm.

*Style length.*—3 cm.

*Style color.*—Yellow 11D.

*Stigma.*—Shape: Oblate. Color: Near Green 143B. Ovary Color: Near RHS Yellow 11D.

OTHER CHARACTERISTICS

Fruits and seeds: Not observed.

Temperature tolerance: Tolerates temperatures from approximately 2° C. to at least 40° C.

Disease/pest resistance: Observed resistance to Ginger blast (*Pyricularia zingiberi*). Neither resistance nor susceptibility to other normal diseases *Hedychium* observed. Neither resistance nor susceptibility to normal pests of *Hedychium* observed.

Drought tolerance: No tolerance for drought.

What is claimed is:

1. A new and distinct cultivar of *Hedychium* plant named 'CHEN XI' as herein illustrated and described.

* * * * *